(12) United States Patent
Goldman et al.

(10) Patent No.: US 8,664,447 B2
(45) Date of Patent: Mar. 4, 2014

(54) PROCESS FOR THE OXIDATION OF HYDROCARBONS WITH THE USE OF IRIDIUM METAL CATALYST COMPLEXES

(75) Inventors: Alan Stuart Goldman, Highland Park, NJ (US); Robert Timothy Stibrany, Long Valley, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 13/611,072

(22) Filed: Sep. 12, 2012

(65) Prior Publication Data

US 2013/0245324 A1 Sep. 19, 2013

Related U.S. Application Data

(60) Provisional application No. 61/533,839, filed on Sep. 13, 2011.

(51) Int. Cl.
*C07C 29/50* (2006.01)
*C07C 46/04* (2006.01)

(52) U.S. Cl.
USPC .......................................... 568/320; 568/910

(58) Field of Classification Search
USPC .................................................. 568/320, 910
See application file for complete search history.

(56) References Cited

U.S. PATENT DOCUMENTS 5,958,821 A 9/1999 Ishii et al.

OTHER PUBLICATIONS

Mas-Marz, E. et al. "Carbene Complexes of Rhodium and Iridium from Tripodal N-Heterocyclic Carbene Ligands: Synthesis and Catalytic Properties", Inorg. Chem., 43: 2213-2219 (2004).
Xu, X. et al., "Synthesis and structural characterization of copper(II) complexes of pincer ligands derived from benzimidazole", Journal of Coordination Chemistry, 60(21): 2297-2308 (2007).

*Primary Examiner* — Sikarl Witherspoon
(74) *Attorney, Agent, or Firm* — Patrick J. Hagan; Dann, Dorfman, Herrell and Skillman, PC

(57) ABSTRACT

Provided is a process for effectively and efficiently oxidizing alkyl-containing molecules with the use of an oxygen-containing gas. An iridium metal catalyst complex with the iridium being coordinated with the nitrogen atoms of a benzimidazolyl-containing ligand is used as the catalyst. The process generates alcohols, ketones and aldehydes directly from alkyl-containing molecules and/or aromatic molecules.

19 Claims, 1 Drawing Sheet

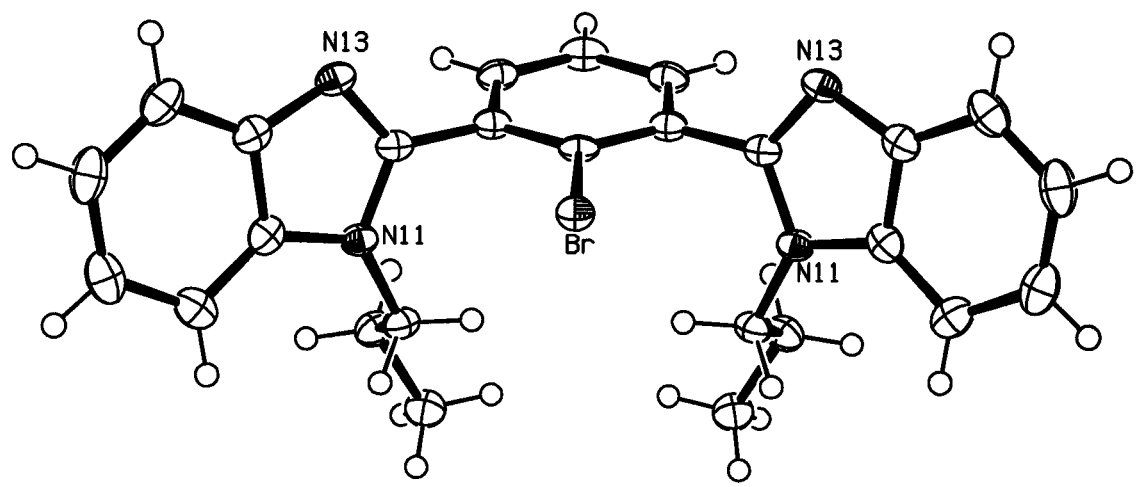

PROCESS FOR THE OXIDATION OF HYDROCARBONS WITH THE USE OF IRIDIUM METAL CATALYST COMPLEXES

CROSS-REFERENCE TO RELATED APPLICATIONS

The present application claims the benefit of U.S. Provisional Patent Application No. 61/533,839, filed Sep. 13, 2011, the entire disclosure of which is incorporated by reference herein.

BACKGROUND OF THE INVENTION

1. Field of the Invention

This invention relates to a process for preparing organic alcohols, aldehydes, and ketones comprising selectively oxidizing alkanes and aromatics using as a catalyst certain iridium complexes. More specifically, the oxidation process involves using an iridium metal catalyst complex with the iridium being coordinated with the nitrogen atoms of a benzimidazolyl-containing ligand.

2. Description of the Related Art

The oxidation of saturated hydrocarbons e.g., alkanes, particularly cycloalkanes, with active oxygen such as molecular oxygen or air to produce the corresponding alcohol, ketone and/or acid reaction product(s), has been an area of research activity for many years in view of the utility and environmental benefits of the reaction to the chemical industry.

There are a number of reports in the literature of various ways to oxidize hydrocarbons to the corresponding aldehyde or ketone. One reference is U.S. Pat. No. 5,958,821 B1 which discloses oxidizing various hydrocarbons such as cycloalkanes, aromatic hydrocarbons, etc. with oxygen in the presence of an oxidation catalyst comprising imide compounds such N-hydroxyphthalimide and a metal compound co-catalyst such as cobalt or manganese acetyl acetonate. The patentee of the '821 reference enumerates virtually every class of known hydrocarbons and virtually every metal in the periodic table.

Other references which have addressed the oxygenation of alkanes include Shun-Ichi Murahashi et al. in *J. Chem. Soc., Chem. Commun.*, (1993) 139-140 in which the authors present results for the oxidation of alkanes and alkenes with oxygen in the presence of aldehydes and using a copper compound catalyst. Their results showed that linear alkanes such as N-decane had extremely low conversion. In *Catalysis Letters* 8 (1991), 45-52 the same authors have shown that isobutane can react with oxygen in the presence of an iron perhaloporphyrin complex to give mostly tert-butyl alcohol.

Shun-Ichi Murahashi et al. have reported in *Tetrahedron Letters*, vol. 34(8), (1993) 1299-1302, the ruthenium catalyzed oxidation of alkanes with alkyl hydroperoxide. Specifically, they reacted n-heptane and n-decane to provide ketones and alcohols., G. P. Khirnova et al. in *Petrol. Chem. U.S.R.R.* vol. 21(1), 49-52 (1981) have reported the liquid phase oxidation of isobutane using a heterogeneous catalyst containing cobalt and molybdenum borides or molybdenum carbides. The main products of this reaction were tert-butyl hydroperoxides, tert-butyl alcohol and acetone. It has also been shown in U.S. Pat. No. 5,395,980 B1 that isobutane can be converted to tert-butyl hydroperoxide at elevated temperatures (about 140° C.) by reacting it with oxygen in the presence of tert-butyl alcohol and di(tert-butyl) peroxide.

There are also reports of the oxidation of alkanes with oxygen using N-hydroxyphthalimide (NHPI) as a catalyst and a metal compound co-catalyst. For example, Y. Ishii et al. in *Catalysis Surveys from Japan* 3 (1999) 27-35 report the oxidation of various alkanes including isobutane. The isobutane gave tert-butyl alcohol and acetone and tert-butyl hydroperoxide. The other alkanes which were tested were all branched alkanes. No results are presented for the oxidation of n-butane using NHPI as the catalyst. Ishii et al. in *J. Org. Chem.* (1996) 61, 4520-4526 present results of the oxidation of various cycloalkanes using NHPI and $Co(acac)_n$. Results are also presented for the oxidation n-octane to give octanols and octanones.

The research continues in this area. Improved processes and more effective catalysts for the processes would be of great benefit to the industry.

SUMMARY OF THE INVENTION

Provided is a process for effectively and efficiently oxidizing alkyl-containing molecules and aromatics with the use of an oxygen-containing gas. An iridium metal catalyst is used as the catalyst. In the catalyst complex, the iridium is coordinated with the nitrogen atoms of a benzimidazolyl-containing ligand. The process generates alcohols, ketones and aldehydes, or a mixture thereof, directly from the alkyl-containing molecules and/or aromatic molecules.

BRIEF DESCRIPTION OF THE FIGURE OF THE DRAWING

The FIGURE shows one embodiment of the crystal structure of 2,2'-(2-bromo-1,3-phenylene)bis(1-propylbenzimidazol-2-yl).

DETAILED DESCRIPTION OF THE INVENTION

This invention relates to a process for preparing organic alcohols, aldehydes, and ketones comprising selectively oxidizing alkanes and aromatics using as a catalyst certain iridium complexes. The iridium catalyst complex involves the iridium being coordinated with the nitrogen atoms of a benzimidazolyl-containing ligand. Use of this Ir catalyst is effective and provides good selectivity.

The alkane starting materials can include straight and branched-chain compounds having from about 1-20 carbon atoms. In one embodiment, the alkane has 1-10 carbon atoms, and more preferably 1-8, such as methane, ethane, propane, n-butane, isobutane, n-pentane, n-hexane, 2-methylpentane, 3-methylpentane, heptane, 2-methylheptane, 3-methylheptane and the like.

The alkane reactant can also comprise a cycloalkane, where the term "cycloalkane" as used herein should be understood to include macrocyclic cycloalkanes having a carbon ring of 8 or more and up to 25 members, and simple cycloalkanes having a carbon ring of less than 8 members but greater than 4 members e.g., cyclopentane, cyclohexane. Typically, the cycloalkane is a C5 to C20 membered ring.

Suitable cycloalkanes for use in the process described herein include, for example, cyclopentane, cyclohexane, cycloheptane, cyclooctane, cyclononane, cyclodecane, cycloundecane, cyclododecane, cyclotridecane, cyclotetradecane, cyclopentadecane, cyclohexadecane, cyclooctadecane, cyclononadecane, cycloicosane, cyclodocosane or cyclotetracosane.

These alkane compounds, if desired, may be substituted with various moieties, although care should be taken to exclude substituents which will adversely affect the activity of the catalyst.

The aromatic starting material can be any suitable aryl compound, such as benzene or naphthalene. It is preferred the aromatic compounds are unsubstituted. Alkyl substituted aromatic compounds, e.g., toluene, ortho-xylene and para-xylene, can also be used, but the alkyl substituent group would generally be oxidized to an alcohol, aldehyde or ketone group, or mixture thereof.

The process of the present invention is carried out in either a homogeneous system or as a supported catalyst in a heterogeneous system. The oxidation is carried out using an oxygen containing gas such as oxygen diluted with argon or nitrogen, or air. The amount of oxygen in the oxygen containing gas can vary. The oxidation may be carried out using a neat substrate such as a $C_2$-$C_{20}$ linear alkane. Methane may be oxidized under pressure in a solvent such as benzene or perfluoromethylcyclohexane.

The catalyst is an iridium metal complex, which can be used with or without an activating cocatalyst. More specifically, the invention is based on the reaction of iridium with a tridentate ligand. In one embodiment, the ligand is a benzimidazolyl-containing ligand. The Ir metal is generally coordinated with the nitrogen atoms in the benzimidazolyl-containing ligands to form an NCN pincer ligand complex. Furthermore, by controlling temperature, catalyst loading, ligand structure, and residence time, product selectivity can be adjusted.

The iridium catalyst complex can be of the formula $LMX(X')_n$ where n=0, 1 or 2, X and X' are independently selected from the group consisting of halides, hydride, triflate, acetates, borates, $C_1$ through $C_{12}$ alky, $C_1$ through $C_{12}$ alkoxy, $C_3$ through $C_{12}$ cycloalkyl, $C_3$ through $C_{12}$ cycloalkoxy, $C_6$ through $C_{14}$ aryl, $C_7$ through $C_{17}$ aralkyl, and olefins including diolefins. M is iridium. L is a nitrogen-containing ligand having two or more nitrogen atoms and in particular a benzimidazolyl-containing ligand. In a preferred embodiment L has the formula

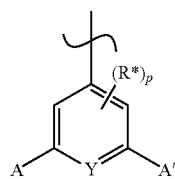

wherein A and A' are independently selected from the group consisting of;

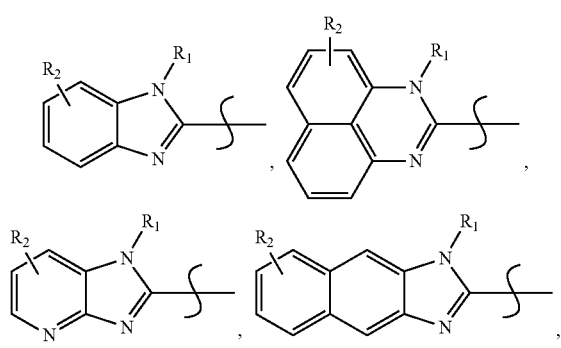

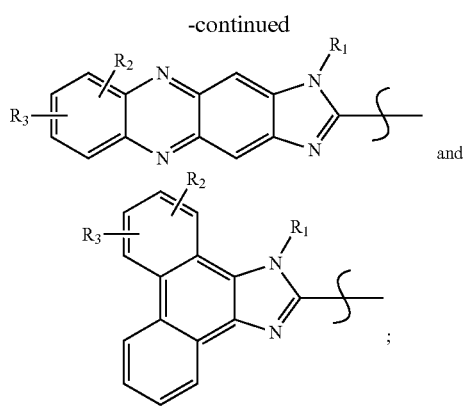

$R_1$, $R_2$, $R_3$ and R* are independently selected from the group consisting of halides, hydride, triflate, acetates, borates, $C_1$ through $C_{12}$ alky, $C_1$ through $C_{12}$ alkoxy, $C_3$ through $C_{12}$ cycloalkyl, $C_3$ through $C_{12}$ cycloalkoxy, $C_6$ through $C_{14}$ aryl, $C_7$ through $C_{17}$ aralkyl and olefins;

and Y is selected from the group consisting of C—H, C—Cl, C—Br, C—I, N, P, C—$OR_4$, wherein $R_4$ is hydrogen, an optionally substituted acyl group, e.g. acetyl or trifluoroacetyl, or an optionally substituted alkylsulfonyl group, e.g. methylsulfonyl or trifluoromethylsulfonyl and other leaving group; and p=0, 1 or 2.

The nitrogen-containing ligands can be synthesized using techniques well known to those skilled in the art. See, for example, U.S. Pat. Nos. 6,037,297; 6,689,928 and U.S. patent application Ser. No. 13/611,089 ("Novel Iridium Catalyst Complexes and C—H Bond Activated Products Therefrom," of Alan Stuart Goldman and Robert Timothy Stibrany, filed concurrently with the subject application), all of the foregoing documents being specifically incorporated herein by reference in their entirety. In general, the noel metal complex can be synthesized by reacting complexing Ir salts with the ligands. This can be accomplished, for example, by dissolving the iridium salt in a solvent, and then adding the ligand. The mixture is then refluxed and cooled. The FIGURE depicts such a ligand.

The iridium catalyst composition having the formula $LMX(X')_n$, as defined above, can also be used with an activating cocatalyst. The activating cocatalyst is selected from the group consisting of alkylalumoxanes, aluminum alkyls, aluminum halides, alkyl aluminum halides, Lewis acids such as tris(pentafluorophenyl)borane, alkylating agents, hydrides such as lithium hydride, reducing agents such as Na/K amalgam, and mixtures thereof. The preferred ratio of metal complex to activating cocatalyst is from $1:10^{-2}$ to $1:10^6$.

The iridium catalyst composition can be supported. When used, the support material maybe a porous material, which includes, but is not limited to, inorganic oxides, zeolites, and inorganic chlorides. The support may also be resinous materials such as polystyrene, polyolefin, and other polymeric materials. These catalysts maybe physiosorbed on the support or chemically bonded to the support.

Generally, the oxidation reaction may be accomplished utilizing conventional temperatures and pressures as used in the prior art. More specifically, temperature ranges from −100 to 250° C. and at pressures from about 5 to 30000 psig are acceptable. The most preferred temperature range is from 0 to 210° C., while the preferred pressure is about 15 to 2000 psig.

Furthermore, the oxidation may take place in a solvent, neat (e.g., no solvent and liquid condensed olefin), or in gas phase (e.g., alkane in gas phase and catalyst in solid phase).

When oxidation is conducted in a solvent phase, the solvent is generally an unreactive polar solvent such as water, acetic acid, acetonitrile, benzonitrile, chlorobenzenes, and the like. Generally, any suitable solvents can be used. Solvents will generally yield a single phase homogeneous system.

The resulting products are generally organic alcohols, aldehydes, and ketones, or a mixture thereof. Such products are valuable chemicals to the industry, which may be used commercially or in research. Use of the present Ir catalyst complex where the Ir is coordinated with the benzimidazolyl-containing ligands has been found effective in catalyzing the oxidation reaction, with good selectivity. Special activity has been found where iridium is coordinated with the benzimidazolyl-containing ligands.

The following examples are provided to further illustrate the present invention, but are not meant to be limiting.

EXAMPLE 1

Preparation of Catalyst A

In an Ar glove box, 91 mg of 2,2'-(2-bromo-1,3-phenylene) bis(1-propylbenzimidazol-2-yl) (0.19 mmol), depicted in the FIGURE, was placed in a 100 ml round bottom flask. Then 64 mg of Ir(COD)Cl (0.19 mmol Ir) was also added to the flask. The flask was sealed with a septa. 20 mL of anhydrous tetrahydrofuran (THF) was needle transferred into the flask to give an orange-brown solution. The flask was then degassed with hydrogen for 5 min. and was left under 10 kPa positive pressure. The flask was then cooled in an ethyl acetate/liquid nitrogen slush. Then 200 ul of 1.6M methyl lithium in diethyl ether was added. This mixture was then allowed to slowly warm to room temperature with stirring. After stirring for 1 hour a cherry solution had formed. This solution was left to stir at room temperature overnight. After stirring overnight the solution appeared dark-purple-black with some dark precipitate. The volatiles were removed under high vacuum to give an amorphous black solid which was stored in an Ar glove box.

EXAMPLE 2

Oxidation of Decane

A 125 ml round bottom flask with a side arm was fitted with a polytetrafluoroethylene (PTFE) needle air inlet. Then 4.0 mg of catalyst A was added to the flask, followed by the addition of 20 ml of purified n-decane to give a very pale-yellow solution with some suspended solid. The flask was fitted with a condenser and was immersed in an oil bath at 110° C. An air flow (bubbling into the solution) of about 20 ml/min. was established. A high rate of stirring was established and the mixture was left to react. After 94 hrs. of reaction time the solution was analyzed by gas chromatography (GC) to contain 3.17 wt. % decanol, 0.40 wt. % 1-decanol, and 4.90 wt. % (2-decanol+3-decanol+4-decanol+5-decanol).

EXAMPLE 3

Oxidation of Benzene

In an Ar glove box, a 30 mL autoclave was loaded with 4.0 mg of [Ir[(κ³N,C,N) 2,2'-(1,3-phenylene)bis(1-propylbenzimidazol-2-yl)]hydridobromide]$_2$ and 5.0 mL of benzene. The autoclave was sealed and taken and charged with 65 psig of air. The autoclave was then placed in an oil bath at 120° C. After equilibration the pressure was 85 psig. After 92 hrs. the autoclave was cooled to room temperature. The pressure at room temperature was 50 psig. The yellow solution was collected and was analyzed by GC to give 0.04% benzoquinone in benzene.

Various modifications and alterations of this invention will become apparent to those skilled in the art without departing from the scope and spirit of the invention. Other objects and advantages will become apparent to those skilled in the art from a review of the preceding description.

A number of patent documents and non-patent documents are cited in the foregoing specification in order to describe the state of the art to which this invention pertains. The entire disclosure of each of the cited documents is incorporated by reference herein.

Furthermore, the transitional terms "comprising", "consisting essentially of" and "consisting of", when used in the appended claims, in original and amended form, serve to indicate what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All iridium catalyst complexes and methods of use thereof that embody the present invention can, in alternate embodiments, be more specifically defined by any of the transitional terms "comprising", "consisting essentially of" and "consisting of".

That which is claimed is:

1. A process for oxidizing alkanes and/or aromatics, which comprises contacting the alkanes and/or aromatics with oxygen in the presence of an iridium catalyst complex comprising iridium complexed with a benzimidazolyl-containing ligand.

2. The process of claim 1, wherein the complex is of the formula LMX(X')$_n$, where n=0, 1 or 2;

X and X' are independently selected from the group consisting of halides, hydride, triflate, acetates, borates, $C_1$ through $C_{12}$ alkyl, $C_1$ through $C_{12}$ alkoxy, $C_3$ through $C_{12}$ cycloalkyl, $C_3$ through $C_{12}$ cycloalkoxy, $C_6$ through $C_{14}$ aryl, $C_7$ through $C_{17}$ aralkyl and olefins;

M is iridium; and

L is a benzimidazolyl-containing ligand.

3. The process of claim 2, wherein L has the formula

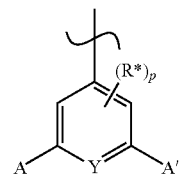

wherein A and A' are independently selected from the group consisting of;

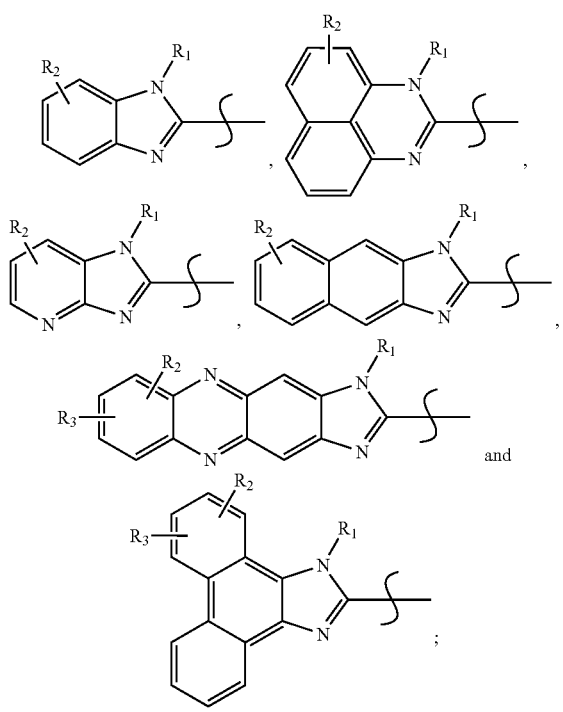

$R_1$, $R_2$, $R_3$ and $R^*$ are independently selected from the group consisting of halides, hydride, triflate, acetates, borates, $C_1$ through $C_{12}$ alky, $C_1$ through $C_{12}$ alkoxy, $C_3$ through $C_{12}$ cycloalkyl, $C_3$ through $C_{12}$ cycloalkoxy, $C_6$ through $C_{14}$ aryl, $C_7$ through $C_{17}$ aralkyl and olefins;

and Y is selected from the group consisting of C—H, C—Cl, C—Br, C—I, N, P, C—OR$_4$, wherein $R_4$ is hydrogen, an optionally substituted acyl group, an optionally substituted alkylsulfonyl group or other leaving group; and p=0, 1 or 2.

4. The process of claim 2, wherein the benzimidazolyl-containing ligand is 2,2'-(1,3-phenylene)bis(1-propylbenzimidazol-2-yl).

5. The process of claim 1, wherein the iridium is coordinated with the nitrogen atoms in the benzimidazolyl-containing ligand to form an NCN pincer ligand complex.

6. The process of claim 1, wherein the iridium catalyst complex is used in combination with a co-catalyst.

7. The process of claim 1, wherein the process comprises oxidizing an alkane.

8. The process of claim 7, wherein the alkane is a $C_2$-$C_{20}$ alkane.

9. The process of claim 8, wherein the alkane is a straight chain alkane.

10. The process of claim 8, wherein the alkane is a branched chain alkane.

11. The process of claim 7, wherein the alkane is a cycloalkane.

12. The process of claim 1, wherein the process comprises oxidizing an aromatic compound.

13. The process of claim 12, wherein the aromatic compound is benzene.

14. The process of claim 12, wherein the aromatic compound comprises a naphthalene.

15. The process of claim 1, wherein the oxidation reaction is carried out in a homogeneous system.

16. The process of claim 1, wherein the oxidation is carried out using an oxygen containing gas.

17. The process of claim 16, wherein the oxygen containing gas comprises air.

18. The process of claim 1, wherein the oxidation reaction is carried out at a temperature in the range of from 0 to 210° C.

19. The process of claim 1, wherein the oxidation reaction is carried out at a pressure in the range of from 15 to 2000 psig.

* * * * *